United States Patent
Lai et al.

(10) Patent No.: US 10,506,224 B2
(45) Date of Patent: Dec. 10, 2019

(54) HOLOGRAPHIC THREE DIMENSIONAL IMAGING PROJECTING MEDICAL APPARATUS

(71) Applicant: ORIENTAL INSTITUTE OF TECHNOLOGY, New Taipei (TW)

(72) Inventors: Chin-Lun Lai, New Taipei (TW); Yu-Mei Chang, New Taipei (TW)

(73) Assignee: ORIENTAL INSTITUTE OF TECHNOLOGY, New Taipei (TW)

( * ) Notice: Subject to any disclaimer, the term of this patent is extended or adjusted under 35 U.S.C. 154(b) by 73 days.

(21) Appl. No.: 15/806,046

(22) Filed: Nov. 7, 2017

(65) Prior Publication Data

US 2019/0141309 A1     May 9, 2019

(51) Int. Cl.
*H04N 13/398* (2018.01)
*A61B 90/00* (2016.01)
*G03B 35/18* (2006.01)

(52) U.S. Cl.
CPC .......... *H04N 13/398* (2018.05); *A61B 90/37* (2016.02); *G03B 35/18* (2013.01)

(58) Field of Classification Search
CPC ....... H04N 13/398; A61B 90/37; G03B 35/18
USPC ........................................................... 348/40
See application file for complete search history.

(56) References Cited

U.S. PATENT DOCUMENTS

| | | | | |
|---|---|---|---|---|
| 5,346,334 A | * | 9/1994 | Einaru ................. | B23Q 9/0014 405/262 |
| 2004/0189813 A1 | * | 9/2004 | Tanaka ................ | H04N 1/2112 348/207.99 |
| 2012/0236269 A1 | * | 9/2012 | Yoneno .................. | G03B 21/28 353/99 |
| 2014/0104577 A1 | * | 4/2014 | Kaneda ............. | G02B 27/2292 353/7 |
| 2014/0143733 A1 | * | 5/2014 | Jung ................... | G06F 3/04815 715/848 |
| 2015/0212333 A1 | * | 7/2015 | Goulanian ........... | H04N 13/305 353/7 |
| 2017/0169436 A1 | * | 6/2017 | Ur .......................... | G05B 15/02 |
| 2017/0228104 A1 | * | 8/2017 | Ziraknejad ............ | G06F 3/0425 |

* cited by examiner

*Primary Examiner* — Mohammed S Rahaman
*Assistant Examiner* — Jimmy S Lee
(74) *Attorney, Agent, or Firm* — Muncy, Geissler, Olds & Lowe, P.C.

(57) ABSTRACT

A holographic three dimensional imaging projecting medical apparatus is provided, including: a three dimensional imaging device, having a projecting mechanism and an image forming mechanism, the projecting mechanism including a housing and a projecting unit, the projecting unit projecting a plurality of projected images through the housing to the image forming mechanism, to form a three dimensional image within an image forming space of the image forming mechanism, the housing having a plurality of reflection portions, each of the plurality of reflection portions having a through hole and a plurality of light reflecting sheets disposed around the through hole, the projecting unit attached to the housing; a motion detector, detecting an operating gesture and generating a control signal corresponding to the operating gesture; and a processor, receiving the control signal and controlling the three dimensional image according to the control signal.

6 Claims, 6 Drawing Sheets

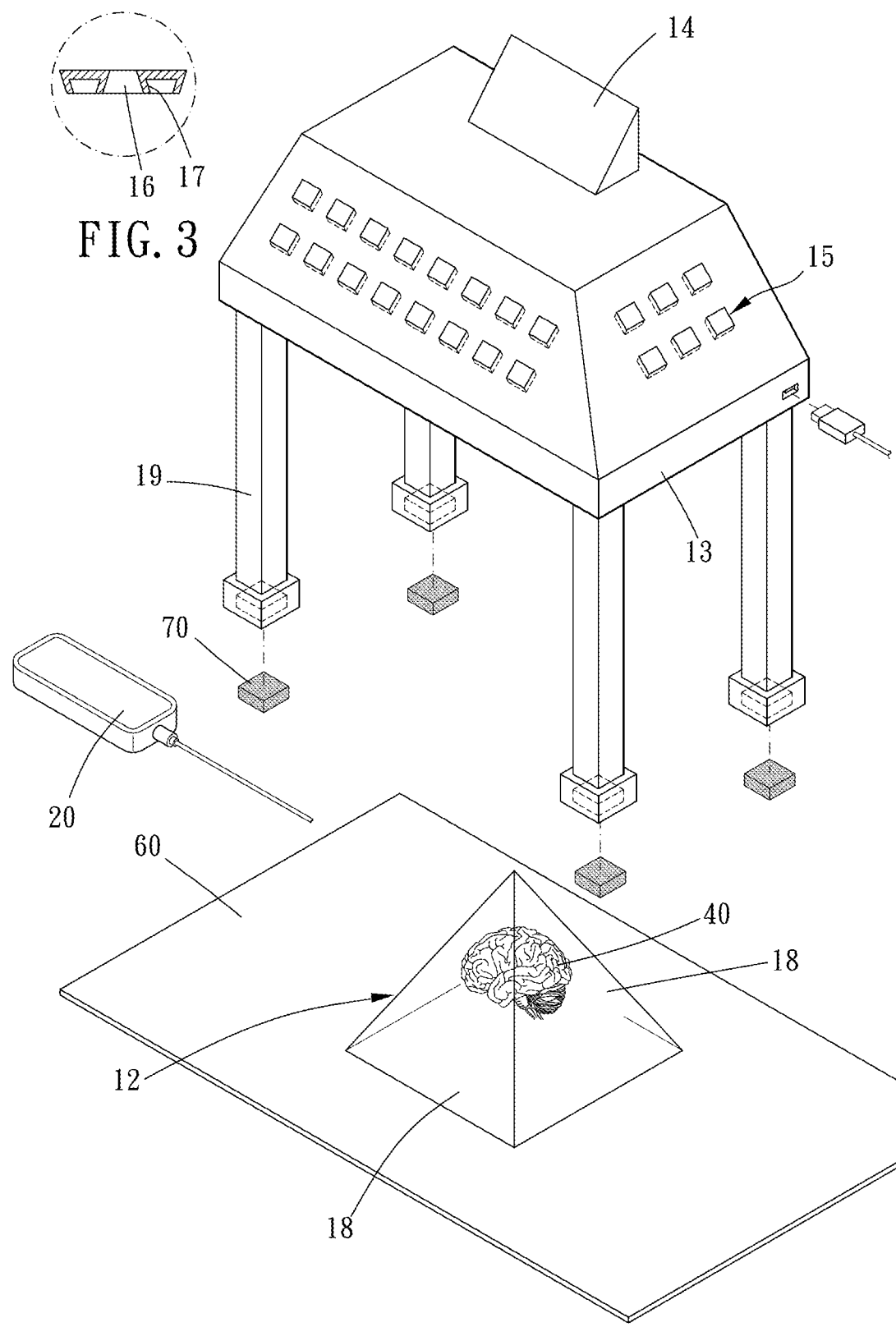

HOLOGRAPHIC THREE DIMENSIONAL IMAGING PROJECTING MEDICAL APPARATUS

BACKGROUND OF THE INVENTION

Field of the Invention

The present invention relates to an image projecting device, especially a holographic three dimensional imaging projecting medical apparatus.

Description of the Prior Art

Conventional health education instruction and medical simulation mostly use a digital flat panel, an entity model, etc. in general instruction mode. Thus, there is a limitation of the conventional health education instruction and medical simulation; for instance, the digital flat panel can only display for one direction, and the entity model can be only operated by few people. Moreover, if using a conventional computer to execute the health education instruction or the medical simulation, users must use a mouse or keyboard to communicate with computer. Thereby, it is not only user-unfriendly, but also has learning limited.

The present invention is, therefore, arisen to obviate or at least mitigate the above mentioned disadvantages.

SUMMARY OF THE INVENTION

An object of the present invention is to provide a holographic three dimensional imaging projecting medical apparatus, in which the holographic three dimensional imaging projecting medical apparatus is configured to be controlled intuitively a three dimensional projected image.

To achieve the above and other objects, a holographic three dimensional imaging projecting medical apparatus is provided, including: a three dimensional imaging device, having a projecting mechanism and an image forming mechanism, the projecting mechanism including a housing and a projecting unit, the projecting unit projecting a plurality of projected images through the housing to the image forming mechanism, to form a three dimensional image within an image forming space of the image forming mechanism, the housing having a plurality of reflection portions, each of the plurality of reflection portions having a through hole and a plurality of light reflecting sheets disposed around the through hole, the projecting unit attached to the housing; a motion detector, detecting an operating gesture and generating a control signal corresponding to the operating gesture; and a processor, receiving the control signal and controlling the three dimensional image according to the control signal.

The present invention will become more obvious from the following description when taken in connection with the accompanying drawings, which show, for purpose of illustrations only, the preferred embodiment(s) in accordance with the present invention.

BRIEF DESCRIPTION OF THE DRAWINGS

FIG. 2 is a breakdown view of a preferable embodiment of the present invention;

FIG. 3 is a partially-enlarged view of FIG. 2;

DETAILED DESCRIPTION OF THE PREFERRED EMBODIMENTS

Figure 1:
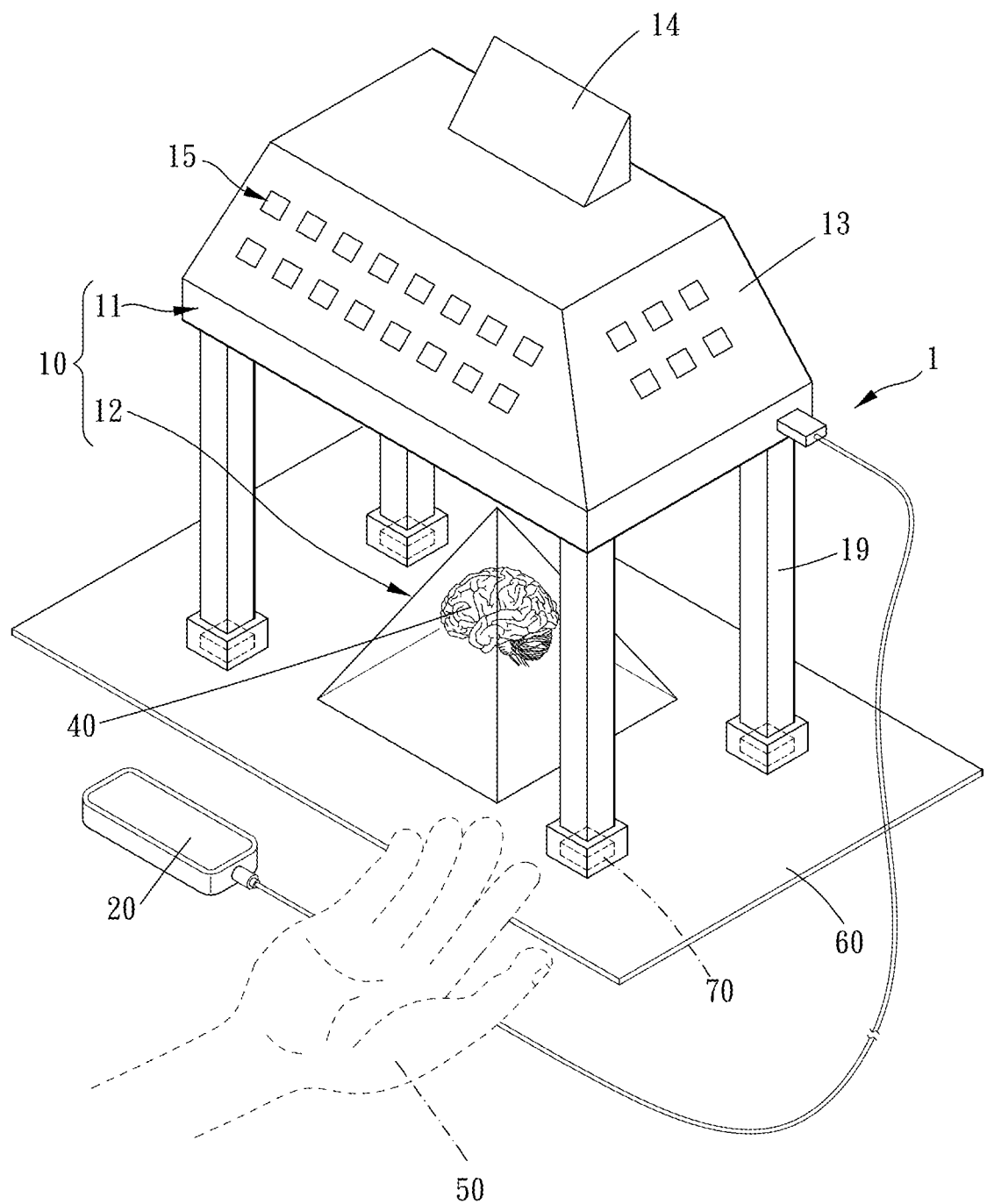
FIG. 1 is a perspective view of a holographic three dimensional imaging projecting medical apparatus according to a preferred embodiment of the present invention.
Figure 4:
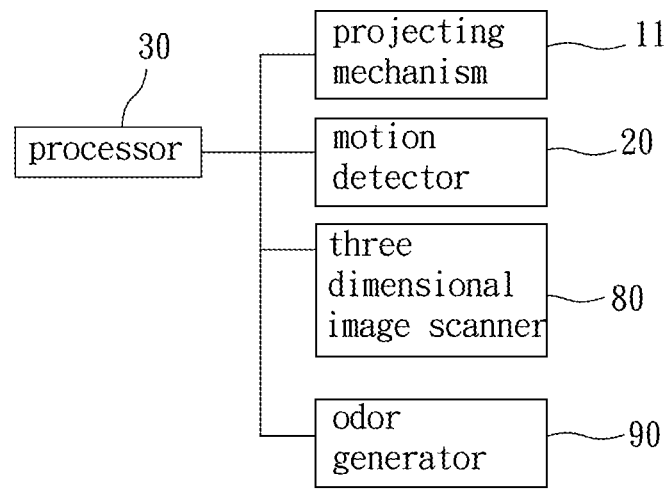
FIG. 4 is a block diagram of a preferable embodiment of the present invention.
Figure 5:
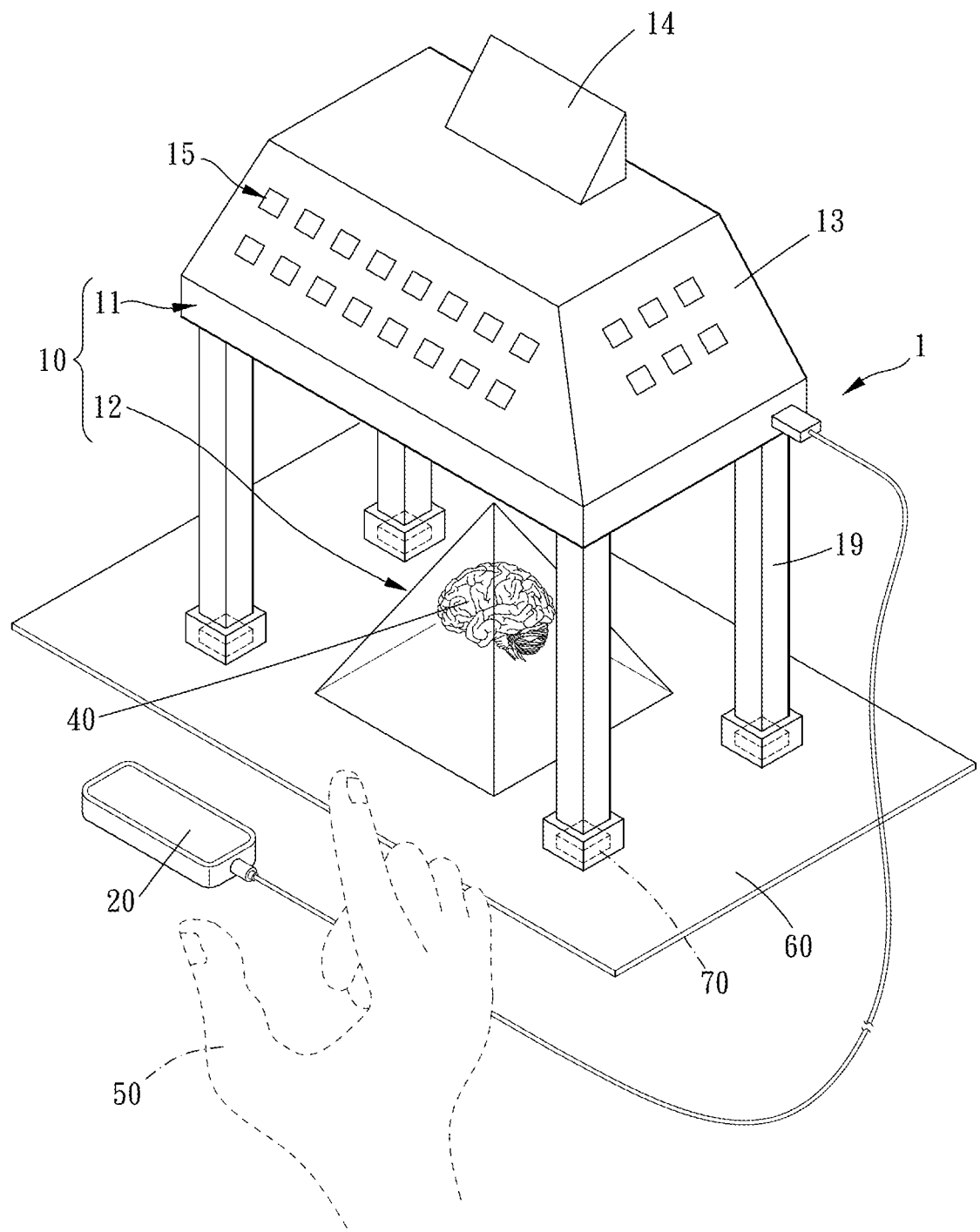
FIG. 5 is a drawing showing a preferable embodiment of the present invention in use.
Figure 6:
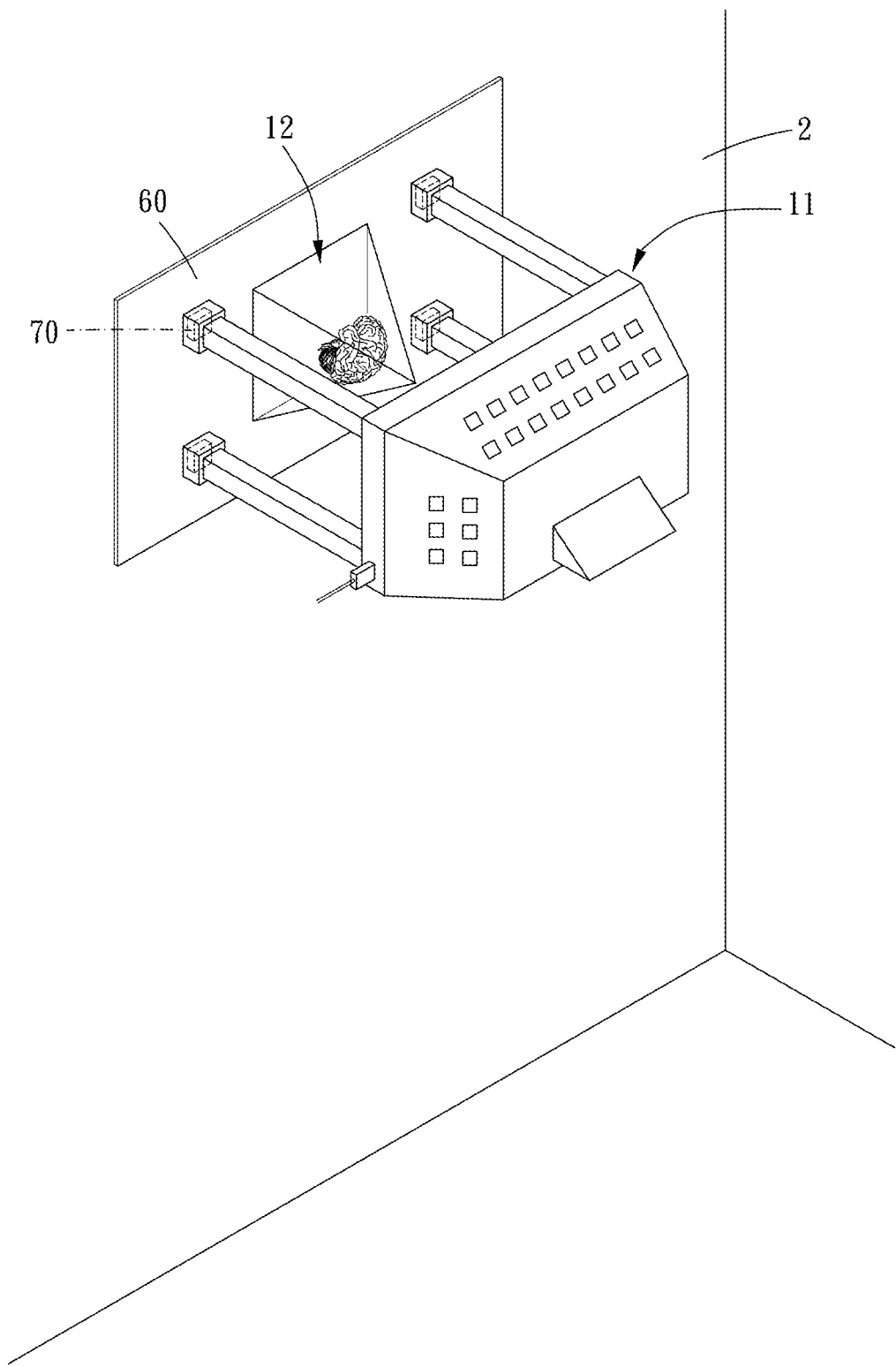
FIG. 6 is another drawing showing a preferable embodiment of the present invention in use.
Figure 7:
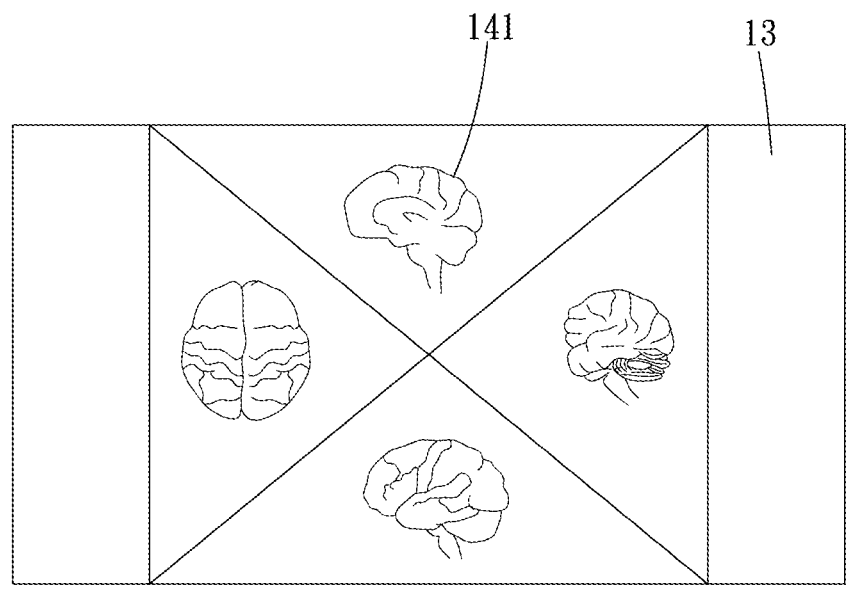
FIG. 7 is a drawing showing a preferable embodiment of a projecting unit projecting a plurality of projected images through a housing.

FIGS. 1-7 show a holographic three dimensional imaging projecting medical apparatus according to a preferred embodiment of the present invention. The holographic three dimensional imaging projecting medical apparatus 1 includes a three dimensional imaging device 10, a motion detector 20 and a processor 30.

The three dimensional imaging device 10 includes a projecting mechanism 11 and an image forming mechanism 12. The projecting mechanism 11 includes a housing 13 and a projecting unit 14. The housing 13 is made of metal material. The projecting unit 14 projects a plurality of projected images 141 through the image forming mechanism 12, to form a three dimensional image 40 within an image forming space of the image forming mechanism 12, the plurality of projected images 141 such as two dimensional images converted from various angle views of a three dimensional article. The housing 13 has a plurality of reflection portions 15, each of the plurality of the reflection portions 15 has a through hole 16 and a plurality of light reflecting sheets 17 is disposed around the through hole 16. In this embodiment, the through hole 16 penetrates through the housing 13, so as to reflect the light and dissipate the heat. The projecting unit 14 is attached to the housing 13. The plurality of light reflecting sheets 17 can reduce the energy consumption generated from the projecting unit 14, and improve the clarity of the projected images 141. In this embodiment, the plurality of reflection portions 15 is disposed on the peripheral of housing 13. Besides, the housing 13 has a light through face 131 which is configured to be passed through the plurality of projected images 141.

The motion detector 20 detects an operating gesture 50 and generates a control signal corresponding to the operating gesture 50. In this embodiment the motion detector 20 is an instant gesture detector, and can detect, track, and save the characteristic of hands such as positions of hand, angles, moving directions of hand, positions of fingertips, etc. without touch. Thus, users can operate the three dimensional image 40 to rotate, zoom, move, and separate elements of the three dimensional image 40, etc. via the operating gesture 50. The operating gesture 50 can be a movement of the palm of the hand, fingers, and other portion of body.

The processor 30 receives the control signal and controls the three dimensional image 40 according to the control signal. Specifically, the processor 30 can change all of the projected images 141, or only change part of the projected images 141. Thereby, the users can operate directly the three dimensional image 40 and view the three dimensional image 40 from different directions.

The plurality of light reflecting sheets 17 respectively protrude inwardly from the housing 13. In this embodiment, the projecting unit 14 further a defines projecting direction toward the image forming mechanism 12, each of the plurality of light reflecting sheets 17 of each reflection portion 15 is transverse to the projecting direction so as to improve the reflection of the light. In this embodiment, the plurality of reflection portions 15 are arranged in array to even distribution light.

The image forming mechanism 12 includes a plurality of reflection sheets 18, the plurality of reflection sheets 18 is disposed around the image forming space. In this embodiment, the plurality of reflection sheets 18 are connected adjacently with each other to form a pyramid. Each of the plurality of reflection sheets 18 can be a triangle-shaped sheet, or a trapezoid-shaped sheet. In this embodiment, the projecting unit 14 is disposed above the housing 13 so that the plurality of projected images 141 can be projected to the plurality of reflection sheets 18, and reflected and refracted by the plurality of reflection sheets 18 to form the three dimensional image 40. In other embodiments, the projecting unit can be disposed within or peripheral of the housing 13. In addition, each of the plurality of reflection sheets 18 is made of photosensitive material. Moreover, each of the plurality of reflection sheets 18 has a photosensitive surface which is a vacuum magnetron sputter coating with a high transmittance (99.99%) and a high reflection rate.

Preferably, the motion detector 20 is detachably electrically connected to the processor 30 so as to carry, store, and adjust the position of the motion detector 20 easily. Furthermore, the motion detector 20 can be communicated with the processor 30 by wire or wireless.

The three dimensional imaging device 10 further includes a plurality of stands 19, the plurality of stands 19 are respectively connected with the housing 13, so as to support the projecting mechanism 11 stably. In this embodiment, each of the plurality of stands 19 is a stud so as to strong the strength of the structure, and improve durability.

The three dimensional imaging device 10 further includes a board body 60, the image forming mechanism 12 is disposed on the board body 60, the projecting mechanism 11 is detachably disposed on the board body 60, each of the plurality stands 19 has a magnetic member 70, so as to attached to a magentically-attractable element. Thus, the three dimensional imaging device 10 can be positionally attached in a support face 2 (such as horizontal support face or vertical support face) in various angles, so as to display in various directions. Preferably, the board body 60 is made of metal material so that the magnetic member 70 is positionally attachable to the board body 60 and does not liable to move.

Besides, the holographic three dimensional imaging projecting medical apparatus 1 further includes a three dimensional image scanner 80, the three dimensional image scanner 80 is for scanning a three dimensional article to form a three dimensional scanned image, the processor 30 receives the three dimensional scanned image and converts the three dimensional scanned image to the plurality of projected images 141.

Furthermore, the holographic three dimensional imaging projecting medical apparatus 1 further includes an odor generator 90, the processor 30 generates an odor signal according to the operating gesture 50, the odor generator 90 receives the odor signal and ejecting an odor which is corresponding to the odor signal such as blood smell, scent, etc., so as to improve an experiencing the scene ambiance in operation.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A holographic three dimensional imaging projecting medical apparatus, including:
   a three dimensional imaging device, having a projecting mechanism and an image forming mechanism, the projecting mechanism including a housing and a projecting unit, the projecting unit projecting a plurality of projected images through the housing to the image forming mechanism, to form a three dimensional image within an image forming space of the image forming mechanism, the housing having a plurality of reflection portions, each of the plurality of reflection portions having a through hole and a plurality of light reflecting sheets disposed around the through hole, the projecting unit attached to the housing;
   a motion detector, configured for detecting an operating gesture and generating a control signal corresponding to the operating gesture; and
   a processor, receiving the control signal and controlling the three dimensional image according to the control signal;
   wherein the image forming mechanism includes a plurality of reflection sheets, and the plurality of reflection sheets disposed around the image forming space;
   wherein the three dimensional imaging device further includes a plurality of stands, and the plurality of stands are respectively connected with the housing; the three dimensional imaging device further includes a board body, the image forming mechanism is disposed on the board body, the projecting mechanism is detachably disposed on the board body, and each of the plurality stands has a magnetic member;
   wherein the plurality of reflection sheets are connected adjacently with each other to form a pyramid; each of the plurality of reflection sheets is made of photosensitive material; the projecting unit further defines a projecting direction toward the image forming mechanism, each of the plurality of light reflecting sheets of each reflection portion is transverse to the projecting direction; the board body is made of metal material; the holographic three dimensional imaging projecting medical apparatus further includes a three dimensional image scanner, the three dimensional image scanner is for scanning a three dimensional article to form a three dimensional scanned image, the processor receives the three dimensional scanned image and converts the three dimensional scanned image to the plurality of projected images; the plurality of reflection portions are arranged in array; and the housing is made of metal material.

2. The holographic three dimensional imaging projecting medical apparatus of claim 1, wherein the motion detector is detachably electrically connected to the processor.

3. The holographic three dimensional imaging projecting medical apparatus of claim 1, wherein the plurality of light reflecting sheets respectively protrude inwardly from the housing.

4. The holographic three dimensional imaging projecting medical apparatus of claim 1, wherein the projecting mechanism is disposed above the image forming mechanism.

5. The holographic three dimensional imaging projecting medical apparatus of claim 1, wherein the projecting unit further defines a projecting direction toward the image forming mechanism, and each of the plurality of light reflecting sheets of each reflection portion is transverse to the projecting direction.

6. The holographic three dimensional imaging projecting medical apparatus of claim 1, further including an odor generator, the processor generating an odor signal according to the operating gesture, and the odor generator receiving the odor signal and ejecting an odor which is corresponding to the odor signal.

* * * * *